(12) United States Patent
Barr et al.

(10) Patent No.: US 9,262,587 B2
(45) Date of Patent: Feb. 16, 2016

(54) SYSTEMS AND METHODS FOR COLLECTING MEDICAL IMAGES

(75) Inventors: David Barr, Seattle, WA (US); Wayne Ellsworth, Seattle, WA (US)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 164 days.

(21) Appl. No.: 13/336,397

(22) Filed: Dec. 23, 2011

(65) Prior Publication Data

US 2013/0163834 A1 Jun. 27, 2013

(51) Int. Cl.
*G06K 9/00* (2006.01)
*G06F 19/00* (2011.01)

(52) U.S. Cl.
CPC .......... *G06F 19/3406* (2013.01); *G06F 19/321* (2013.01)

(58) Field of Classification Search
CPC ............................ G06F 19/3406; G06F 19/321
See application file for complete search history.

(56) References Cited

U.S. PATENT DOCUMENTS

| | | | | |
|---|---|---|---|---|
| 6,458,081 B1* | 10/2002 | Matsui et al. | ................. | 600/437 |
| 6,872,179 B2* | 3/2005 | Kamiyama et al. | ........... | 600/437 |
| 6,904,161 B1* | 6/2005 | Becker et al. | ................. | 382/128 |
| 6,953,433 B2* | 10/2005 | Kerby et al. | .................. | 600/443 |
| 7,960,971 B2* | 6/2011 | Feiweier | ....................... | 324/309 |
| 2006/0170714 A1* | 8/2006 | Kanda | ............................... | 346/2 |
| 2008/0072896 A1* | 3/2008 | Setzer et al. | ............. | 128/200.24 |

* cited by examiner

*Primary Examiner* — Long V Le
*Assistant Examiner* — Colin T Sakamoto

(57) ABSTRACT

Disclosed herein are systems and methods for collecting a plurality of medical images. According to one embodiment, a system may include an image acquisition unit to acquire image data, a processing unit to process the image data, a workflow unit to receive a selection of a primary workflow, and an insertion unit to suspend the workflow system. The insertion unit may receive a second selection of a secondary workflow. Upon the completion of the collection of the second plurality of medical images, the workflow unit may resume the collection of the first plurality of medical images. According to certain embodiments, the primary workflow or the secondary workflow may specify an order for collecting a primary and secondary plurality of medical images. Annotations may be added to the plurality of images based on the primary workflow and/or the secondary workflow.

24 Claims, 10 Drawing Sheets

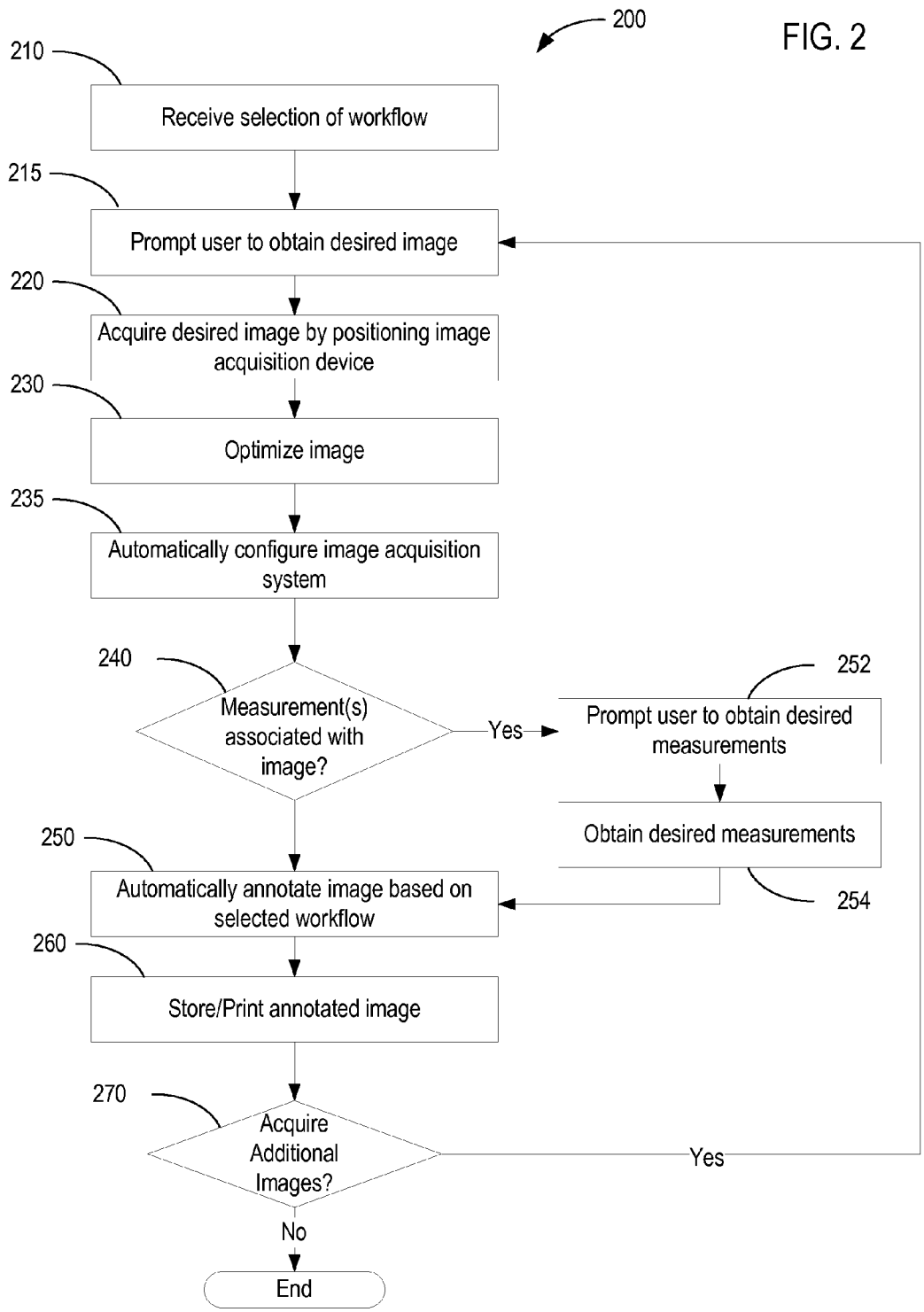

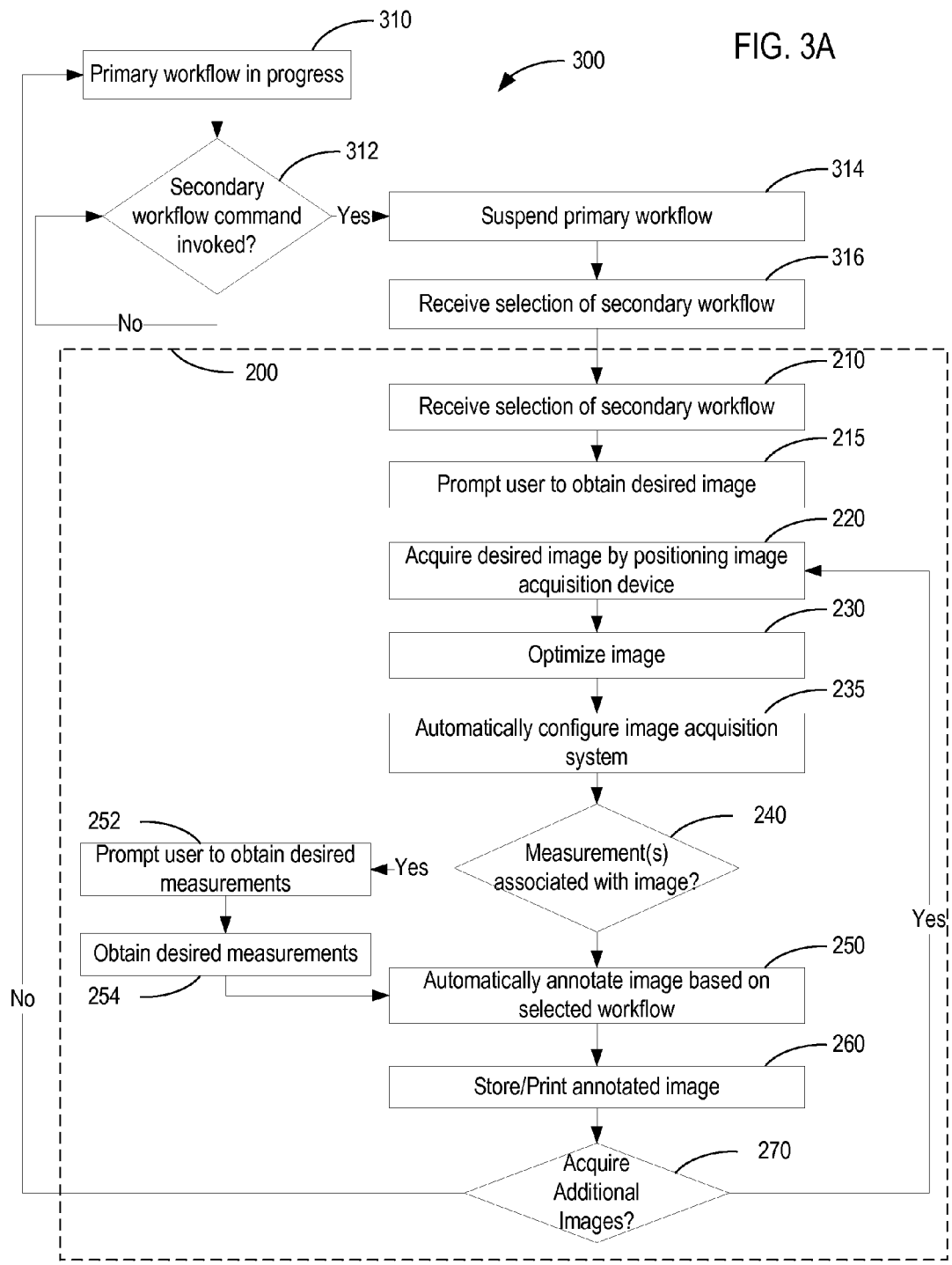

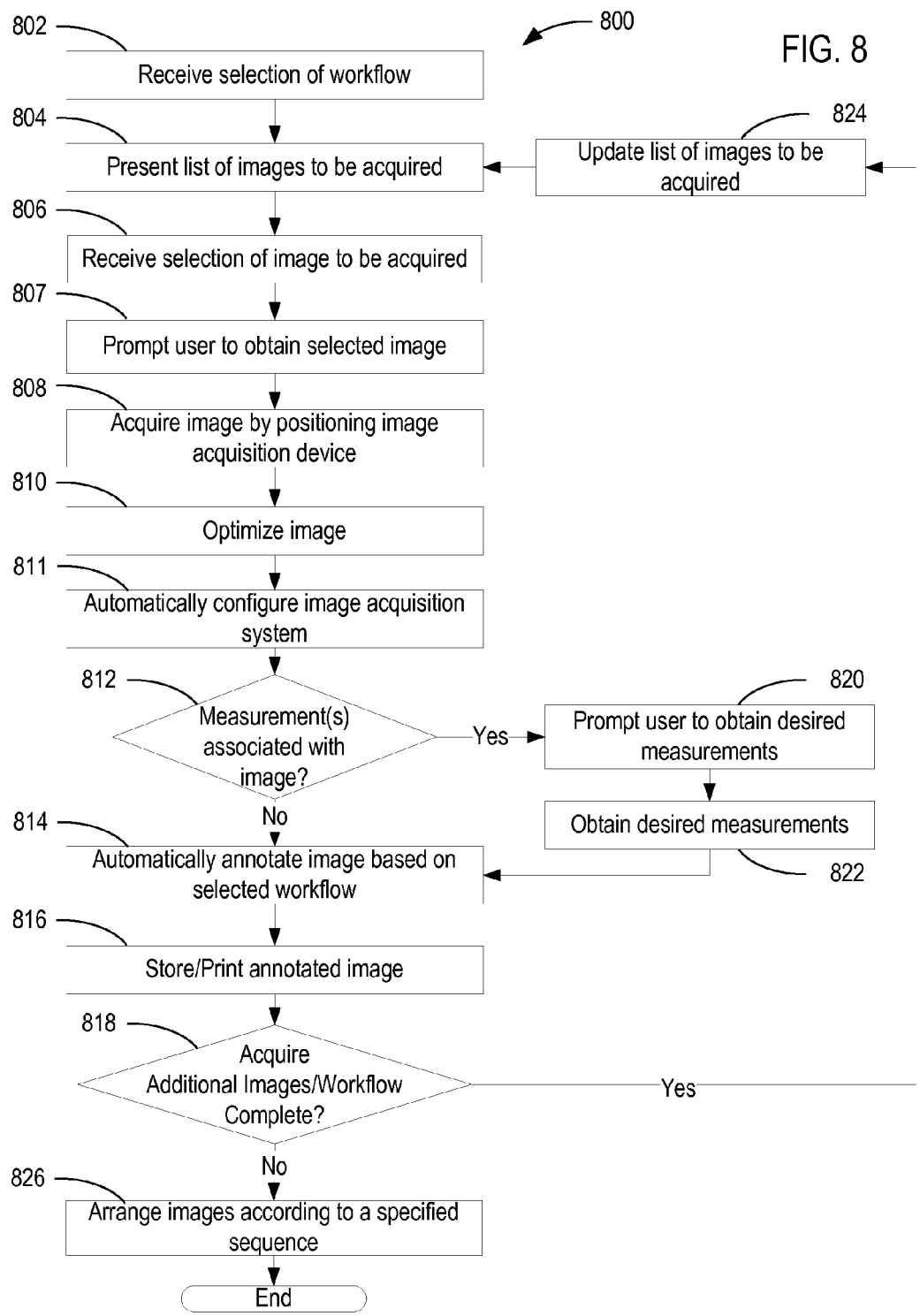

SYSTEMS AND METHODS FOR COLLECTING MEDICAL IMAGES

BRIEF DESCRIPTION OF THE DRAWINGS

FIG. 2 illustrates a flow chart of one embodiment of a method for acquiring a plurality of medical images using a workflow.

FIG. 3A illustrates a flow chart of one embodiment of a method for utilizing a secondary workflow in conjunction with a primary workflow.

FIG. 8 illustrates a flow chart of one embodiment of a method for acquiring a plurality of medical images using a workflow.

DETAILED DESCRIPTION OF PREFERRED EMBODIMENTS

Figure 1:
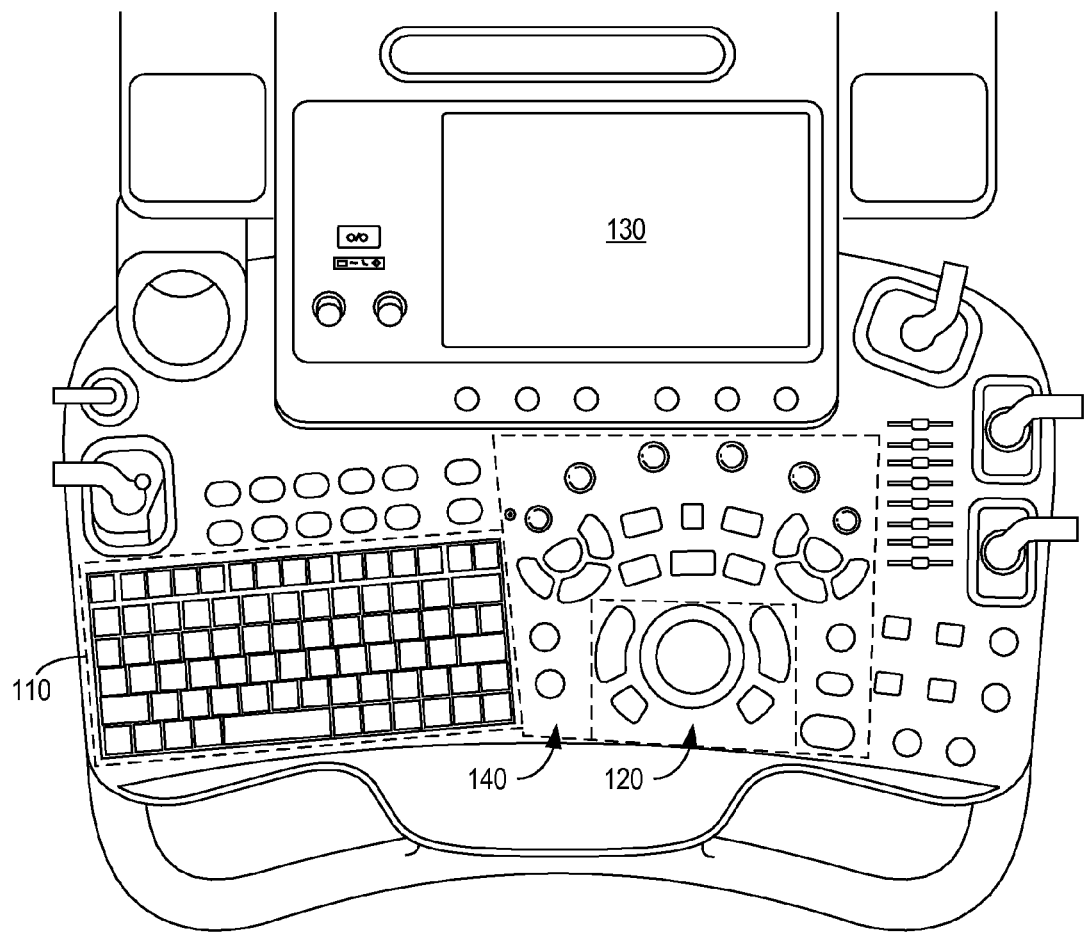
FIG. 1 illustrates a simplified functional block diagram of one embodiment of a system for determining the location of a device on a network.

In connection with a variety of medical imaging applications, a variety of images may be acquired according to a workflow. The images may be collected in a particular order specified by the workflow to facilitate review by a physician. For example, in connection with an ultrasound examination, a particular sequence of images may be specified. Further, in connection with specific types of examinations, specific sequences may be specified (e.g., one sequence may be specified for a cardiac ultrasound examination and another sequence may be specified for an obstetric ultrasound examination). A variety of types of ultrasound examinations may utilize a workflow to standardize the examination. For example, the following ultrasound examinations may be associated with a workflow according to various embodiments disclosed herein: an abdominal examination, a kidney examination, an early obstetrical examination, a late obstetrical examination, a gynecological examination, a thyroid examination, a breast examination, a testicular examination, an adult or pediatric cardiac examination, an upper or lower extremity arterial or venous vascular examination, a carotid vascular examination, etc. According to certain embodiments, workflows may be developed that allow for flexibility in the sequence of image acquisition. For example, a fetal ultrasound examination may involve collecting a plurality of views of the fetus. Certain views may be difficult to obtain while the fetus is in certain positions; however, by allowing for flexibility in the sequence in which the images are acquired, the user may acquire other images while waiting for the fetus to change positions. Even though images may be collected in a flexible sequence, the images may be reordered upon the completion of the workflow to facilitate review of the plurality of images. Workflows may help a user to ensure that each of a large number of images is collected and uniformly processed, even though the sequence of the collection may be variable.

Collection of medical images according to a specified sequence may offer several advantages. For example, workflows may be developed and refined in order to improve the efficiency of the workflow. Further, an operator may develop expertise and familiarity by collecting images using a specified workflow. Reliability may be improved by use of a workflow by requiring that a specified set of images be acquired, and that no images are omitted. This improved reliability may also improve documentation relied upon for legal matters. Use of a workflow may further facilitate training of users by helping users to consistently obtain each medical image specified by a workflow. Use of a workflow may reduce repetitive motion injuries by reducing the number of keystrokes and other repetitive motions an operator must perform during the course of an examination.

Analysis of the plurality of ultrasound images may be improved by providing the plurality of images in a sequence that facilitates analysis. For example, a radiologist or other user interpreting the medical images may develop expertise using a workflow and making diagnoses using a workflow.

Additional benefits may be realized by coupling the use of a primary workflow with secondary workflow that may be invoked by a user on an as needed basis. For example, during a fetal ultrasound examination, a user may identify a particular condition necessitating obtaining additional images relating to the condition. Secondary workflows may be developed for a variety of congenital conditions that may be diagnosed using images in utero (e.g., certain cardiac abnormalities, limb malformations, etc.). According to another example, secondary workflows may be developed to standardize the documentation of unexpected pathology encountered during an examination.

In one example, an ultrasound examination system may include a device for acquiring medical images that a user can manipulate with one hand, thus leaving the user's other hand free for interaction with the ultrasound examination system. In order to facilitate the generation of ultrasound images according to a specified sequence, the system may include a variety of workflows associated with various types of examinations.

A variety of types of automation may be included within a workflow. For example, a workflow may automate changes in an image acquisition mode (e.g., 2D, M-mode, color, power, pulsed wave, steerable continuous wave doppler, compound imaging, tissue doppler imaging). A workflow may also automate the annotation of images collected during course of the workflow. A workflow may automate the collection of various measurements associated with the particular image by automatically selecting a measurement tool for prompting the operator to obtain a desired measurement using a specified measurement tool. In addition, a workflow may provide context aware assistance to a user during a workflow. For example, an on-screen graphic may be displayed to illustrate a location of a patient's body associated with an image to be acquired during one step of a workflow.

Standardized workflows may be utilized in the collection of still images or video clips using a variety of medical imaging technologies. In addition to ultrasound systems, the present disclosure may be adapted for use in connection with other forms of medical imaging, including: magnetic resonance imaging (MRI), positron emission tomography (PET) imaging, x-ray imaging, computed tomography (CT) imaging. Further, while many examples described herein pertain to still images, video images are also contemplated within the scope of the present disclosure.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or detailed description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform the processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of computer-readable media suitable for storing electronic instructions.

FIG. 1 illustrates an ultrasound system 100 that may be utilized in connection with the systems and methods disclosed herein. System 100 may be utilized for gathering a plurality of medical images, such as ultrasound images. A user may select a plurality of workflows that facilitate the collection of a specified plurality of images, which may correspond to a plurality of views of a particular area under examination (e.g., abdomen, heart, thyroid, breast, etc.) or a particular type of examination (e.g., an obstetric examination).

According to one embodiment, a user may progress through the workflow by acquiring images according to a sequence specified by the workflow. The workflow may facilitate the selection of a plurality of images corresponding to a particular feature to be shown in a subset of the plurality of images.

In the course of an examination a user may observe an issue that merits further examination. For example, a user may observe an abnormal growth. The user may temporarily suspend a primary workflow in order to gather one or more images of the growth. The user may invoke a secondary workflow that prompts the user to gather a standardized plurality of images.

According to one embodiment, system 100 may be utilized in a free form mode in which a user does not utilize a workflow. In a free form mode, a user may acquire a desired image using an image acquisition device. Once a desired image has been acquired, the user may freeze the image in order to perform measurements and/or annotations on the image. Annotations may be added using keyboard 110. The user may continue to acquire images until the user has acquired each desired image. While a free-form mode allows for flexibility, the user must annotate each image and must determine which images have been obtained and which images need to be obtained.

A user of system 100 may use one hand to manipulate a control/navigation input 120 and keyboard 110 while using the other hand to operate an image acquisition device (not shown). Since a user may require one hand for manipulating the image acquisition device, it is advantageous to allow a user to perform as much of the examination as possible using a single hand to perform tasks, such as image annotation, making measurements, and directing a workflow. Additional controls 140 may be disposed in proximity to control/navigation input 120. A touch screen 130 may provide an additional user input device that may be used to receive input and to display information to a user.

FIG. 2 illustrates a flow chart of one embodiment of a method 200 for acquiring a plurality of medical images using a workflow. At 210, a selection of a workflow may be received from a user. For example, a user may be able to select one workflow for a breast examination and select another workflow for a cardiac examination. Each workflow may specify a particular sequence for obtaining a specific plurality of medical images. In order to improve the efficiency of collecting and reviewing the plurality of medical images, the workflow may specify a particular sequence for the collection of the plurality of medical images. After the user selection of a workflow is received, the user may be prompted to acquire a desired image at 215. The user may acquire the desired image by positioning an image acquisition device at 220. For example, the user may be prompted to obtain a particular view of a patient's heart (e.g., a view of the patient's pulmonary valve) during a cardiac examination.

At 230, a user may optimize an acquired image. Various optimizations may be performed, including adjustments of contrast or selection of a specific area of interest. A user may turn on or off Doppler coloration, adjust the contrast of the image, or indicate particular areas of interest in the image.

At 235, the image acquisition system may be automatically configured based upon the workflow. For example, a variety of modes of an image acquisition device may be utilized in a single workflow. As described above, in embodiments where the image acquisition device is an ultrasound system, modes may include 2D, M-mode, color, power, pulsed wave, steerable continuous wave doppler, compound imaging, tissue doppler imaging. A particular mode may be specified for each image to be acquired during a workflow, and based upon the mode associated with an image to be acquired, the mode of the image acquisition system may be automatically changed.

At 240, the workflow may determine whether a measurement is to be associated with the image. For example, in a fetal ultrasound examination, a measurement tool may be utilized in connection with various images showing measurements such as the circumference of a fetus's head or abdomen. The workflow may prompt a user to obtain the desired measurements at 252. The user may obtain the desired measurements at 254.

At 250, the image may be automatically annotated based on the selected workflow. As discussed above, in the free-form mode, the user may be required to manually annotate each image. One advantage of using a workflow is that the annotations associated with each image may be specified and automatically added to each acquired image. Automating the annotations may improve the efficiency of the operator and may improve the consistency of the annotations while reducing the potential for operator error.

At 260, the annotated image may be stored or printed for later examination. According to various embodiments, images may be stored digitally, together with annotations, measurements, or other information. According to other embodiments, the annotated image may be printed together with information regarding measurements.

At 270, it may be determined whether additional images are to be acquired based on the selected workflow. If additional images are to be acquired, method 200 may return to 220. If no additional images are to be acquired, method 200 may terminate.

According to one embodiment, a user may interrupt a workflow and resort to a free-form mode in order to investigate conditions or abnormalities discovered during an examination. For example, during a fetal ultrasound examination, a user may identify a condition, such as a malformed limb, that requires the acquisition of additional images relating to the condition. Once the images relating to the condition have been obtained, the user may resume the workflow. While this embodiment allows the user considerable flexibility to investigate conditions or abnormalities discovered during an examination, additional advantages may be realized by allowing a user to select a secondary workflow relating to the identified condition or abnormality.

FIG. 3A illustrates a flow chart of one embodiment of a method 300 for utilizing a secondary workflow in conjunction with a primary workflow. At 310, a primary workflow is in progress. For example, an operator may be conducting an ultrasound examination and in the course of the ultrasound examination, the operator may notice a condition or anomaly that merits investigation and the collection of additional medical images. At 312, it may be determined whether a secondary workflow command has been invoked.

When a secondary workflow command is invoked at 312, the primary workflow is suspended at 314 during the completion of a secondary workflow. At 316, a selection of a secondary workflow may be received. In order to facilitate the selection of a secondary workflow, a user may be presented with a variety of secondary workflows that are related to a primary workflow. For example, during an obstetric ultrasound examination, secondary workflows relating to various birth defects may be presented when a user invokes the secondary workflow command.

Following the selection of a secondary workflow, the secondary workflow may follow method 200 for acquiring a plurality of medical images. A complete discussion of method 200 is included above in connection with the discussion of FIG. 2. According to various embodiments, other methods for the collection of the plurality of images associated with the secondary workflow may be utilized in place of method 200.

Figure 3B:
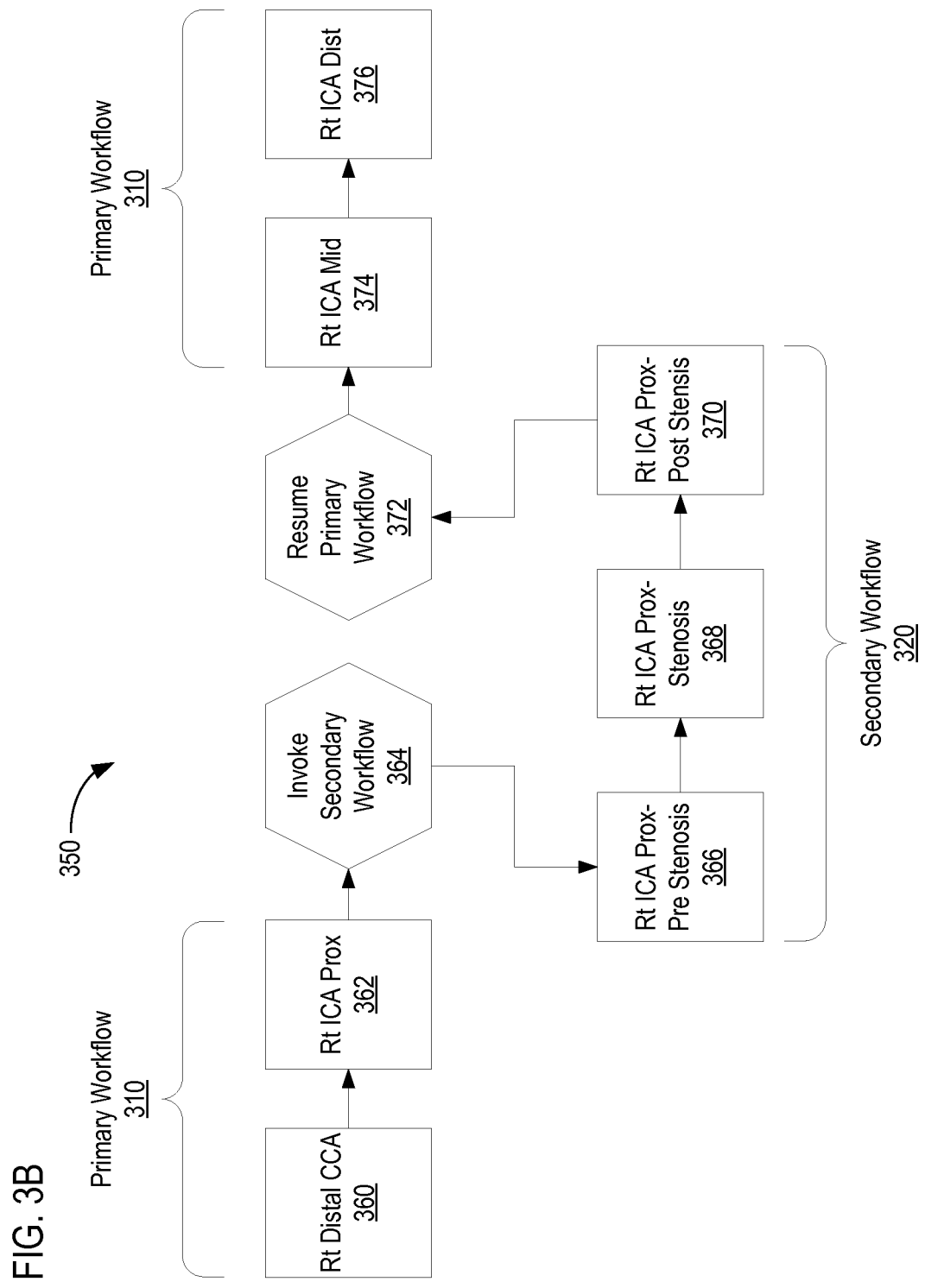
FIG. 3B illustrates a specific example in which a secondary workflow is invoked during a primary workflow to document a stenosis identified in the course of a primary workflow.

FIG. 3B illustrates a specific exemplary workflow 350 that includes a primary workflow 310 and a secondary workflow 320. Primary workflow 310 comprises a portion of a workflow for a carotid vascular examination. Secondary workflow 320 comprises a workflow for a stenosis. At 360, an image may be acquired of a right distal common carotid artery, and at 362, an image may be acquired of a proximal right internal carotid artery. A stenosis may be identified at 362, and accordingly, an operator may invoke a secondary workflow at 364.

Secondary workflow 320 includes three images acquired at 366, 368, and 370 that document the stenosis. In the illustrated embodiment, the stenosis is identified during the acquisition of an image of the right proximal internal carotid artery. Accordingly, each image associated with the stenosis may use the label associated right proximal internal carotid artery, "Rt ICA Prox," as a root and may attach a suffix specific to each image. According to the illustrated embodiment, the suffixes comprise "Pre Stenosis," "Stenosis," and "Post Stenosis." This naming convention, in addition to describing the images associated with the stenosis, also provides an indication of where in the ultrasound examination the stenosis was identified.

Upon the completion of secondary workflow 320, primary workflow 310 may resume 372. According to the illustrated embodiment, two additional images are acquired, namely a right mid internal carotid artery image, at 374, and a right distal internal carotid artery, at 376. As described above, when a secondary workflow is invoked, the primary workflow may be suspended during the completion of the secondary workflow.

Figure 4:
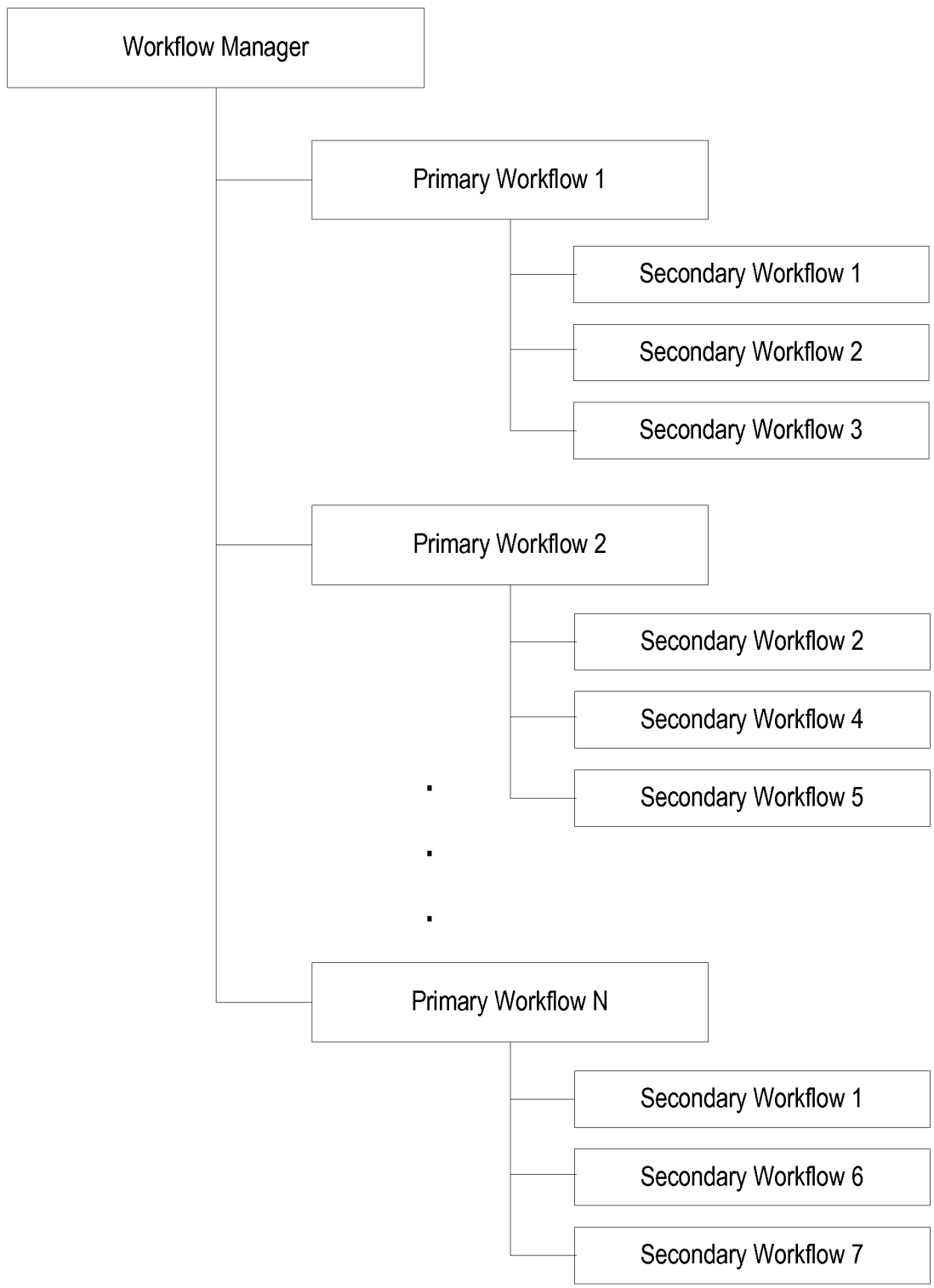
FIG. 4 illustrates a conceptual representation of a plurality of primary workflows and a plurality of secondary workflows.

FIG. 4 illustrates a conceptual representation of a plurality of primary workflows and a plurality of secondary workflows. A user may initially be prompted to select a workflow related to the collection of a desired plurality of medical images. A workflow selection may include a plurality of primary workflows (e.g., Primary Workflow 1, Primary Workflow 2, Primary Workflow N), and the plurality of secondary workflows associated with one or more of the primary workflows. Secondary workflows may relate to one or more primary workflows and may be presented to the user when a primary workflow is interrupted, in order to readily provide access to relevant secondary workflows. The secondary workflows may be structured so as to achieve many of the advantages associated with the use of a primary workflow, while still allowing a user to have considerable flexibility to investigate anomalies discovered during an examination. For example, a secondary workflow associated with a cardiac examination may address a vascular stenosis (i.e., a narrowing of a cardiac blood vessel), stenosis of a cardiac valve (i.e., Aortic Valve, Mitral Valve), or regurgitation of cardiac valves (i.e, Mitral Valve, Aortic Valve, Pulmonic Valve, Tricuspid Valve). Primary workflows associated with abdominal, obstetric, breast, gynecological, or thyroid examinations may be associated with secondary workflows relating to a mass (i.e., an anomalous solid structure) or a cyst (i.e., a fluid filled structure).

Figure 5:
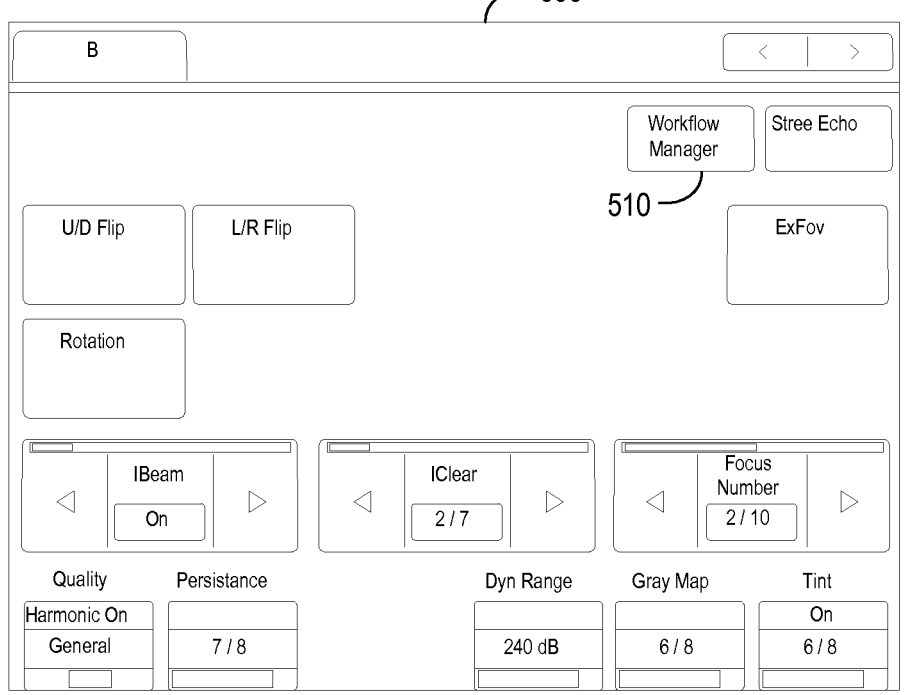
FIG. 5 illustrates a screen shot of a system that may be utilized to facilitate the collection of a plurality of medical images, according to one embodiment.

FIG. 5 illustrates a screen shot 500 of a system that may be utilized to facilitate the collection of a plurality of medical images, according to one embodiment. As illustrated, screenshot 500 allows a user to adjust a variety of settings associated with a system for collecting a plurality of medical images. The illustrated embodiment is an ultrasound system; however, other types of medical imaging systems may be utilized according to various embodiments. Screenshot 500 may be displayed on a touch screen, and a user may select various options using the touch interface. According to other embodiments, a pointing device, such as mouse, may be utilized. As illustrated in FIG. 5, a workflow manager may be invoked using command 510.

Figure 6:
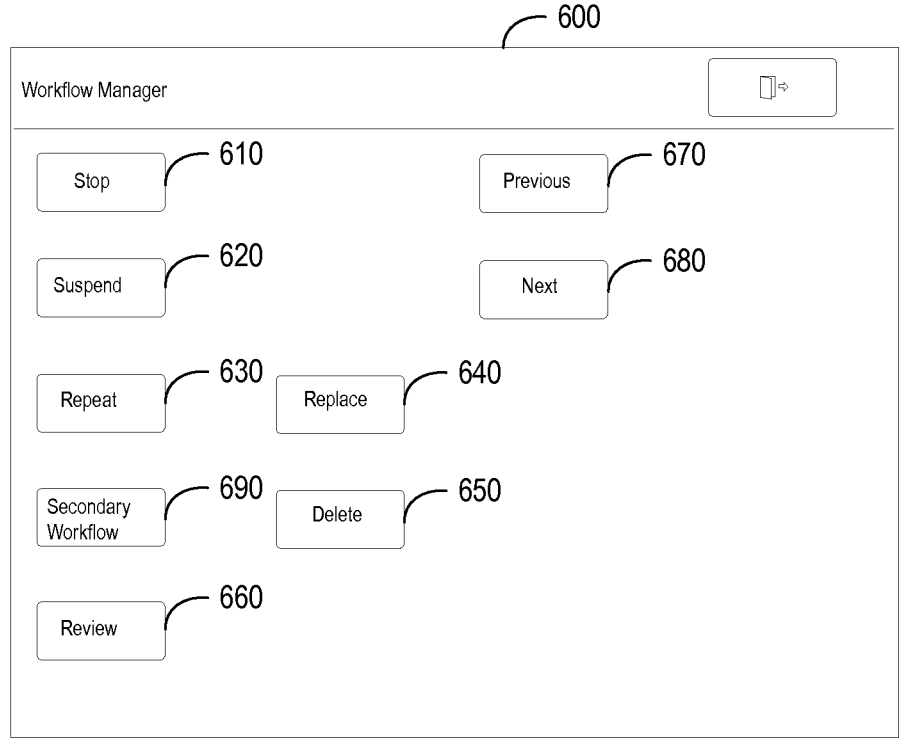
FIG. 6 illustrates a screen shot that displays various options associated with a system for the collection of medical images that may be utilized to control the workflow.

FIG. 6 illustrates a screen shot 600 that displays various options associated with a system for the collection of medical images that may be utilized to control the workflow. A stop command 610 may be utilized to permanently stop a workflow. A suspend command 620 may be utilized to suspend a workflow and operate the image acquisition system in a manual mode. A repeat command 630 may be utilized in order to include additional images associated with a step of a workflow. Other commands, such as a replace command 640, a delete command 650, a review command 660, a previous command 670, and a next command 680 may be utilized to navigate the workflow.

A secondary workflow command 690 may be used to invoke a secondary workflow during a primary workflow. The secondary workflows that are displayed by invoking secondary workflow command 690 may relate to the primary workflows. For example, if the primary workflow is directed toward a breast examination, secondary workflows associated with the primary workflow may relate to conditions that are commonly discovered during a breast examination.

Figure 7A:
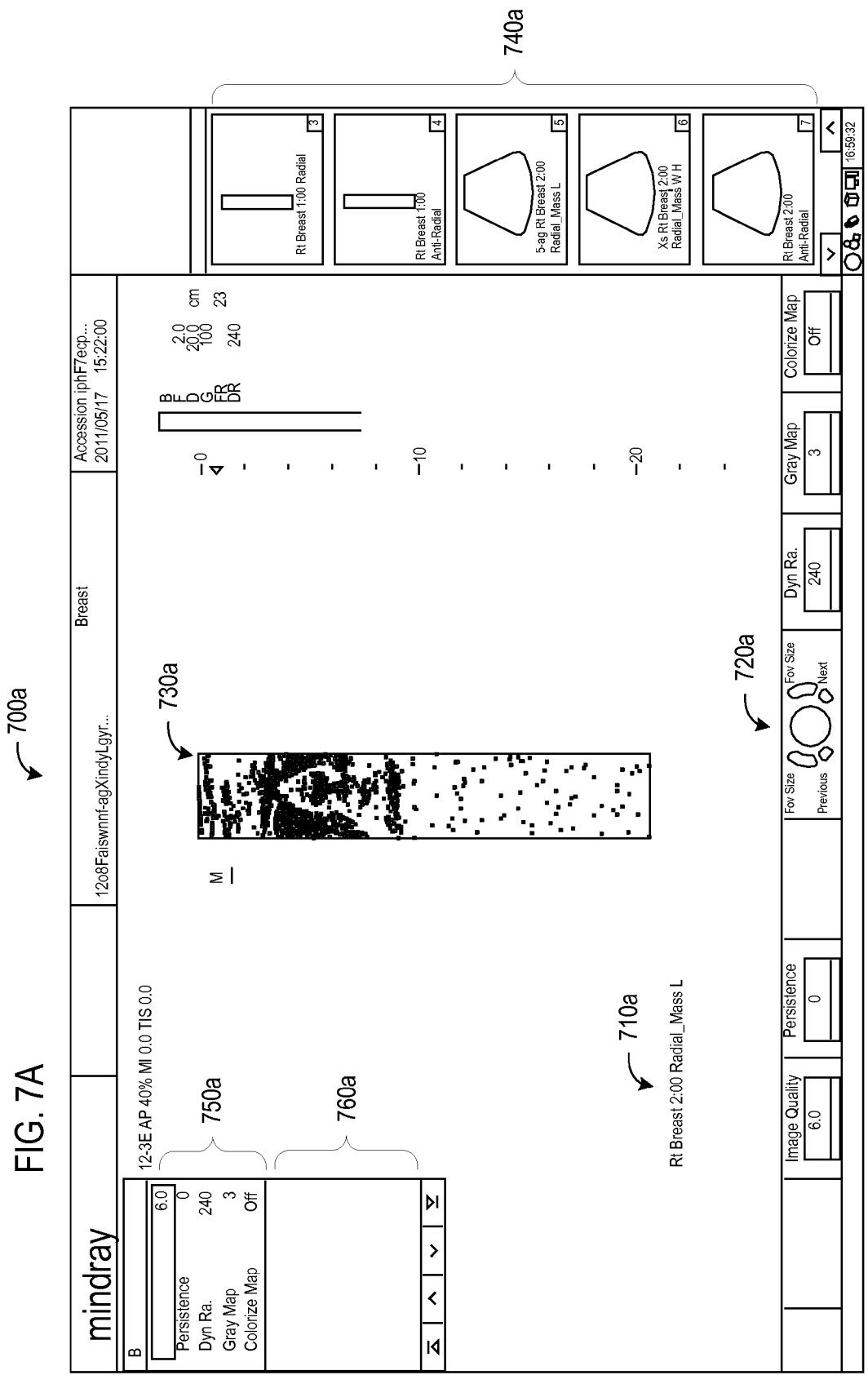
FIG. 7A illustrates a screen shot that may be displayed in connection with a workflow.

FIG. 7A illustrates a screen shot 700a that may be displayed in connection with a workflow. The screen shot may be a part of a workflow relating to breast examination. Screenshot 700a includes an ultrasound display area 730a for displaying an ultrasound image. The image may include a label 710a based on the workflow. As described above, labeling a plurality of images using a workflow may result in greater consistency and efficiency in the collection and subsequent analysis of the plurality of medical images.

A context-sensitive control/navigation indicator 720a may be displayed to provide control/navigation options to a user based on the workflow. According to the embodiment illustrated in FIG. 7A, context-sensitive control/navigation indicator 720a may correspond to a control/navigation input available to a user, such as control/navigation input 120, shown in FIG. 1. In FIG. 7A, context-sensitive control/navigation indicator 720a indicates that the left and right bottom buttons may move between a previous item and a next item in the workflow, while the left and right top buttons adjust the field-of-view (FOV) size. Context-sensitive menu areas 750a and 760a may provide relevant information to a particular action in the workflow or relevant to system settings.

A previously acquired image bar 740a may be provided and may be utilized by a user to return to the previous portion of the workflow. The images displayed in previously acquired image bar 740a may correspond to the sequence in which the images were collected according to a workflow. A user may be able to return to a previous portion of the workflow by selecting an image from previously acquired image bar 740a.

Figure 7B:
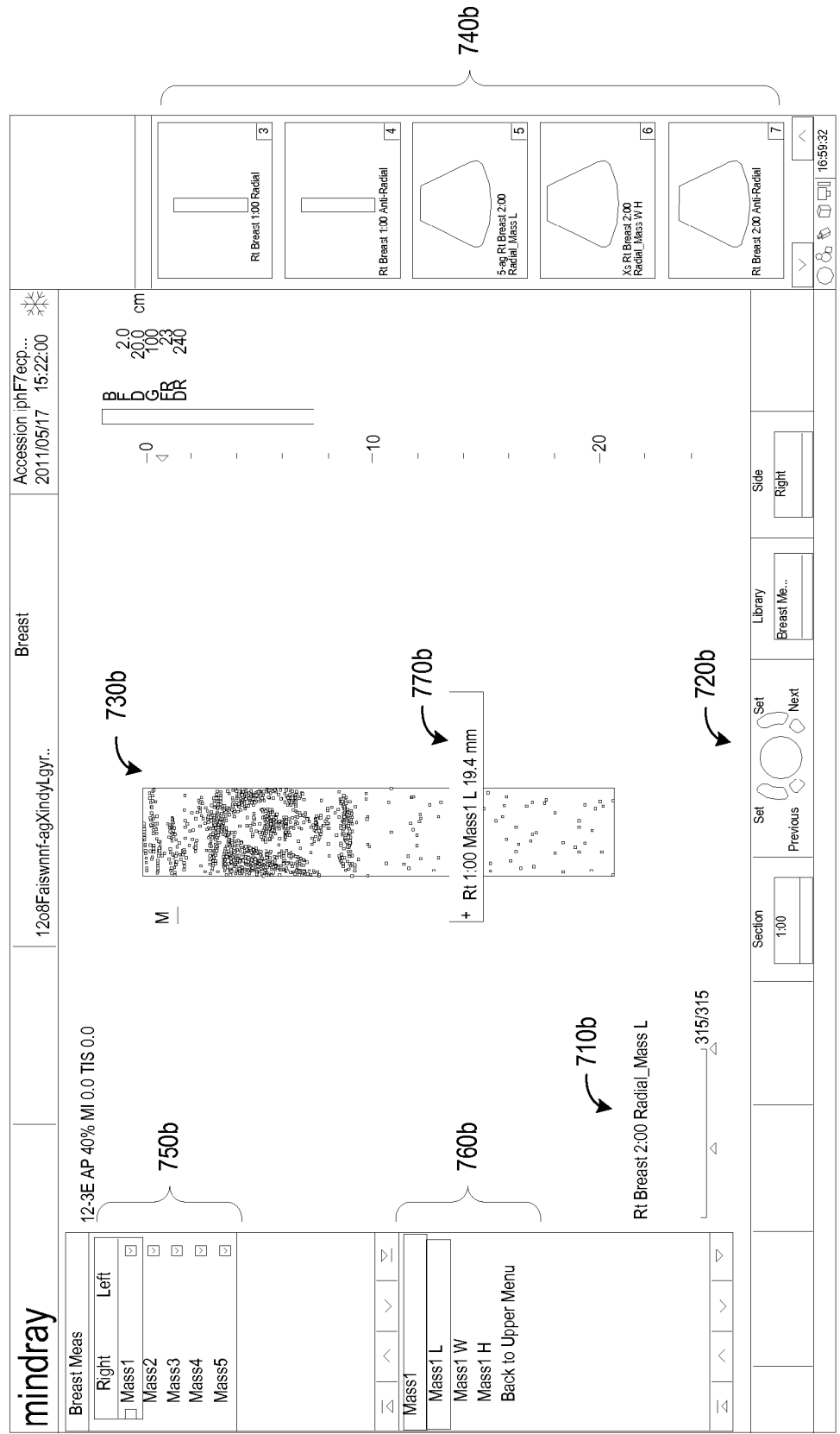
FIG. 7B illustrates a screen shot that may be displayed in connection with a primary or secondary workflow relating to a mass.

FIG. 7B illustrates a screen shot 700b that may be displayed in connection with a primary or secondary workflow relating to a mass. Context sensitive menu areas 750b and 760b display information related to the workflow. Context sensitive area 750b includes a menu allowing for selection of up to five separate masses. An indicator, such as a box, may indicate which mass is currently under examination. Context sensitive area 760b may include various measurements associated with each mass. For example, the length ("L"), width ("W"), and height ("H") may be measured for each mass. A measurement indicator 770b may be shown, and may be utilized by the user in obtaining the desired measurement. An annotation 710b may be added automatically to the image based upon the workflow. Context-sensitive control/navigation indicator 720b may display functions related to the portion of the workflow being completed by the user.

FIG. 8 illustrates a flow chart of one embodiment of a method 800 for acquiring a plurality of medical images using a workflow. At 802, a selection of a workflow may be received from a user. In particular, workflows utilized in connection with method 800 may benefit from flexibility in the sequence of image acquisition. For example, a fetal ultrasound examination may involve collection of a plurality of views of the fetus. Certain views may be difficult to obtain while the fetus is in certain positions. By allowing for flexibility in the sequence in which the images are acquired, the user may acquire other images while waiting for the fetus to change positions. Even though images may be collected in a flexible sequence, the images may be reordered upon the completion of the workflow to facilitate review of the plurality of images.

After the user selection of a workflow is received, a system implementing method 800 may present a user with a list of images to be acquired at 804. At 806, a user may receive a selection of an image to be acquired. At 807, the user may be prompted to obtain the selected image. At 808, a user may acquire an image by positioning an image acquisition device. At 810, a user may optimize an acquired image. Various optimizations may be performed, including adjustments of contrast or selection of a specific area of interest.

At 811, the image acquisition system may be automatically configured based upon the workflow. For example, a variety of modes of an image acquisition device may be utilized in a single workflow. A particular mode may be specified for each image to be acquired during a workflow, and based upon the mode associated with an image to be acquired, the mode of the image acquisition system may be automatically changed.

At 812, the workflow may determine whether a measurement is to be associated with the image. For example, in a fetal ultrasound examination, a measurement tool may be utilized in connection with various images showing measurements such as the circumference of the fetus's head or abdomen. The workflow may prompt a user to obtain the desired measurements, at 820. The user may obtain the desired measurements at 822. At 814, the image may be automatically annotated based on the selected workflow. The annotations may include a label indicating the particular view shown in the image, and/or any measurements associated with the image.

At 816, the annotated image may be stored or printed for later examination. According to various embodiments, images may be stored digitally, together with annotations, measurements, or other information. According to other embodiments, the annotated image may be printed together with information regarding measurements. At 818, it may be determined whether additional images are to be acquired based on the selected workflow and/or whether the workflow is complete. In assessing whether a workflow is complete, a system implementing method 800 may determine whether additional images are included in the selected workflow that are have not yet been acquired. According to certain embodiments, if additional images are included in the selected workflow that have not yet been acquired, the user may be prompted to indicate whether the user wants to return to the workflow to obtain the images, or whether the user desires to exit the workflow without obtaining the images. If additional images are to be acquired, the list of images to be acquired may be updated at 824. If no additional images are to be acquired, the images may be arranged according to a specified sequence, at 826, and method 800 may terminate. As discussed above, certain efficiencies may be realized by presenting the plurality of images according to a radiologist, or other medical professional, according to a particular sequence that may facilitate the review of the plurality of images. Method 800 may be utilized, in various embodiments, with a secondary workflow, as described in connection with FIG. 3A.

Figure 9:
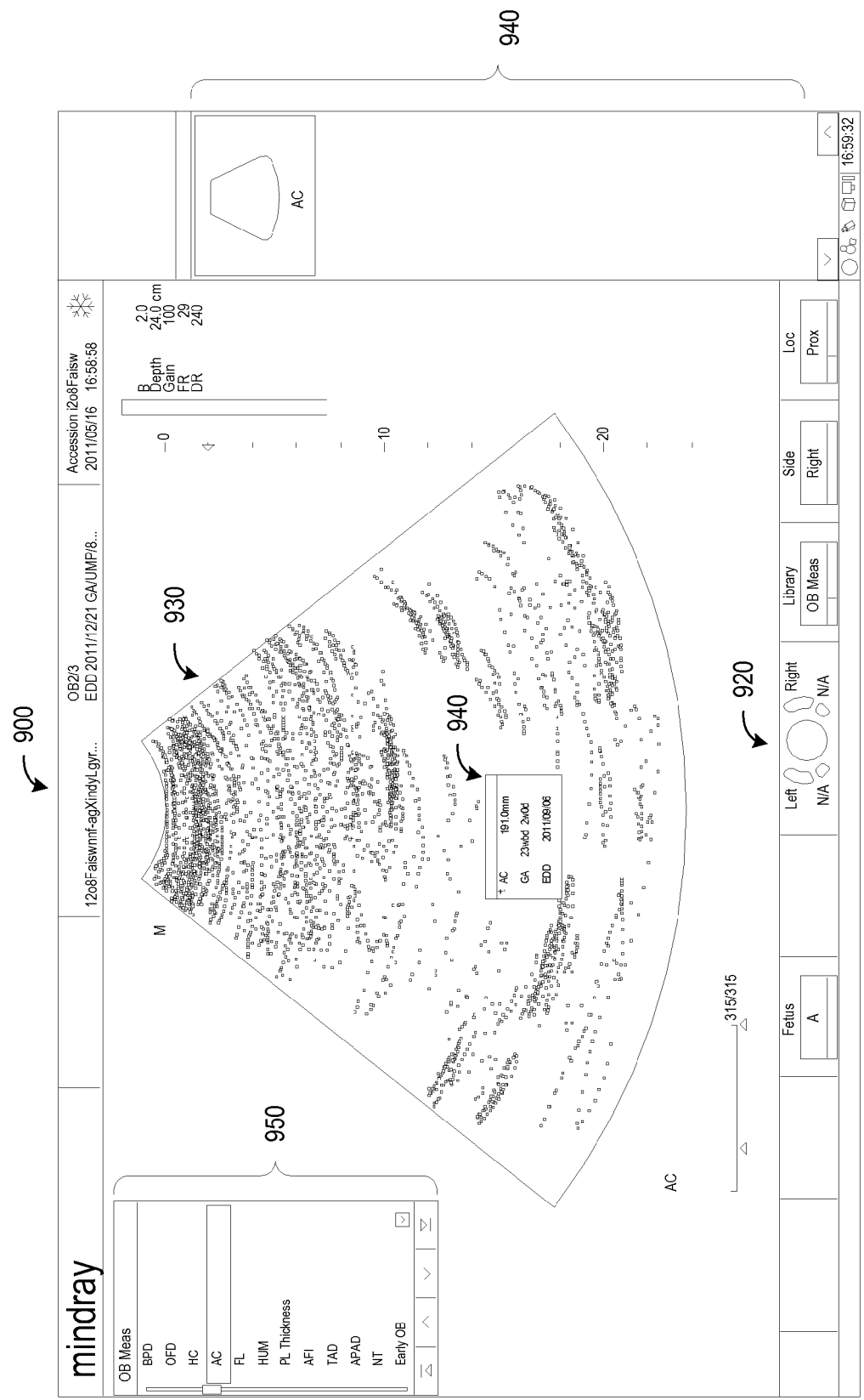
FIG. 9 illustrates a screen shot that may be displayed in connection with a workflow in which a plurality of images may be acquired in a variable sequence.

FIG. 9 illustrates a screen shot 900 that may be displayed in connection with a workflow in which a plurality of images may be acquired in a variable sequence. The screen shot may be a part of a workflow relating to a fetal examination. Screenshot 900 includes an ultrasound display area 930 for displaying an ultrasound image. A context-sensitive control/navigation indicator 920 may be displayed to provide control/navigation options to a user based on the workflow. Context-sensitive control/navigation indicator 920 indicates that the left and right bottom buttons may move between a previous item and a next item in the workflow. A previously acquired image bar 940 may be provided, and may be utilized by a user to return to the previous portion of the workflow. The image displayed in previously acquired image bar 940 may correspond to the sequence in which the images were collected according to a workflow.

Context-sensitive menu areas 950 may provide relevant information to a particular action in the workflow. Context sensitive area 950 includes a menu listing a plurality of images to be acquired. After selecting one of the images displayed in context sensitive area 950, a workflow may annotate the image, and if measurements are associated with the image, may prompt a user to make the associated measurements. According to the illustrated embodiment, a measurement of the abdominal circumference ("AC") is associated with the image. Based on the abdominal circumference, the gestational age ("GA") of the fetus may be determined and displayed, together with the expected date of delivery ("EDD"). According to one embodiment, the list of images displayed in context sensitive area 950 may display only those images that are to be obtained, while those images that have already been obtained are omitted from the list. Accordingly, a user may readily determine whether each image in a specified workflow has been obtained by determining whether context sensitive area 950 includes additional images.

It will be understood by those having skill in the art that many changes may be made to the details of the above-described embodiments without departing from the underlying principles disclosed herein. The scope of the present invention should, therefore, be determined only by the following claims.

The invention claimed is:

1. A system for collecting a plurality of medical images, comprising:
   an image acquisition device to acquire image data;
   a processing unit communicatively coupled with the image acquisition device to process the image data; and
   a memory storing instructions that, when executed by the processing unit, cause the processing unit to:
      receive a first selection of a primary workflow corresponding to a first plurality of medical images for a first type of medical examination, wherein the primary workflow defines a first sequence for the first plurality of medical images, and wherein the primary workflow defines image acquisition settings for the first plurality of medical images;
      collect, using the image acquisition device, one or more images corresponding to the first plurality of medical images;
      suspend the primary workflow in response to a secondary workflow command invoked by a user during the primary workflow and in response to collecting the one or more images corresponding to the first plurality of medical images;
      present, in response to the secondary workflow command, a plurality of secondary workflows associated with the primary workflow for selection by the user;
      receive a second selection of a secondary workflow of the plurality of secondary workflows from the user, the secondary workflow corresponding to a second plurality of medical images for a second type of medical examination different from the first type of medical examination, wherein the secondary workflow defines an image sequence for the second plurality of medical images, and wherein the secondary workflow defines image acquisition settings for the second plurality of medical images;
      collect, using the image acquisition device, the second plurality of medical images; and
      in response to completion of the collection of the second plurality of medical images, resume the collection of the first plurality of medical images.

2. The system of claim 1, wherein the image acquisition device comprises an ultrasound system.

3. The system of claim 1, wherein the primary workflow defines a label identifying a corresponding view or body region for each of the first plurality of medical images and the secondary workflow defines a label identifying a corresponding view or body region for each of the second plurality of medical images, wherein the instructions further cause the processing unit to annotate the first plurality of medical images based on the primary workflow and to annotate the second plurality of medical images based on the secondary workflow.

4. The system of claim 3, wherein the instructions further cause the processing unit to annotate each of the second plurality of medical images using at least a portion of an annotation associated with an image from the first plurality of medical images, wherein the image from the first plurality of medical images is acquired immediately prior to receiving the selection of the secondary workflow.

5. The system of claim 1, wherein the instructions further cause the processing unit to identify at least one of the first plurality of medical images having an associated measurement and to obtain the measurement.

6. The system of claim 1, further comprising a display communicatively coupled with the processing unit to display context sensitive information regarding at least one of the plurality of medical images.

7. The system of claim 6, wherein the context sensitive information comprises an indication describing one of the first plurality of images.

8. The system of claim 6, wherein the context sensitive information comprises a prompt to obtain a measurement based on one of the primary workflow and the secondary workflow.

9. The system of claim 6, wherein the context sensitive information comprises a list of a plurality of secondary workflows.

10. The system of claim 1, wherein the primary workflow defines an image acquisition mode for each of the first plurality of medical images and the secondary workflow defines an image acquisition mode for each of the second plurality of medical images, wherein the instructions further cause the processing unit to automatically control the image acquisition device to operate according to the acquisition mode for a corresponding image based on one or more of the primary work flow and the secondary workflow.

11. The system of claim 1, wherein the memory further stores instructions that cause the processing unit to, in response to completion of the collection of the first plurality of medical images, arrange the first plurality of medical images according to the first sequence defined by the primary workflow for review by a medical professional, and arrange the second plurality of medical images according to the second sequence defined by the secondary workflow for review by a medical professional.

12. A method for collecting a plurality of medical images, comprising:
   receiving a first selection of a primary workflow corresponding to a first plurality of medical images for a first type of medical examination, wherein the primary workflow defines a first sequence for the first plurality of medical images, and wherein the primary workflow defines image acquisition settings for the first plurality of medical images;

collecting, using an image acquisition device, at least one of the first plurality of medical images;

receiving a secondary workflow command during the primary workflow;

suspending the primary workflow in response to receiving the secondary workflow command and in response to collecting the at least one of the first plurality of medical images;

in response to receiving the secondary workflow command, presenting a plurality of secondary workflows associated with the primary workflow for selection by a user;

receiving a second selection of a secondary workflow of the plurality of secondary workflows from the user, the secondary workflow corresponding to a second plurality of medical images for a second type of medical examination different from the first type of medical examination, wherein the secondary workflow defines an image sequence for the second plurality of medical images, and wherein the secondary workflow defines image acquisition settings for the second plurality of medical images;

collecting, using the image acquisition device, the second plurality of medical images; and in response to completion of the collection of the second plurality of medical images, resuming the collection of the first plurality of medical images.

13. The method of claim 12, further comprising collecting the first plurality of images according to the sequence specified by the primary workflow.

14. The method of claim 12, further comprising collecting the second plurality of images according to the sequence specified by the secondary workflow.

15. The method of claim 12, further comprising annotating the first plurality of medical images without user intervention based on the primary workflow and annotating the second plurality of medical images without user intervention based on the secondary workflow.

16. The method of claim 15, further comprising annotating each of the second plurality of medical images using at least a portion of an annotation associated with an image from the first plurality of medical images, wherein the image from the first plurality of medical images is acquired immediately prior to receiving the selection of the secondary workflow.

17. The method of claim 12, further comprising:
identifying at least one of the first plurality of medical images having an associated measurement; and
obtaining the measurement.

18. The method of claim 17, further comprising selecting a measurement instrument without user intervention for obtaining the measurement.

19. The method of claim 12, further comprising displaying context sensitive information regarding at least one of the plurality of medical images.

20. The method of claim 19, wherein the context sensitive information comprises an indication describing one of the first plurality of images.

21. The method of claim 19, wherein the context sensitive information comprises a prompt to obtain a measurement based on one of the primary workflow and the secondary workflow.

22. The method of claim 19, wherein the context sensitive information comprises a list of a plurality of secondary workflows.

23. The method of claim 12, wherein the method further comprises, in response to completion of the collection of the first plurality of medical images, arranging the first plurality of medical images according to the first sequence defined by the primary workflow for review by a medical professional, and arranging the second plurality of medical images according to the second sequence defined by the secondary workflow for review by a medical professional.

24. A non-transitory computer-readable storage medium storing instructions that, when executed by a processor, are configured to cause the processor to perform a method, the method comprising:

receiving a first selection of a primary workflow corresponding to a first plurality of medical images for a first type of medical examination, wherein the primary workflow defines a first sequence for the first plurality of medical images, and wherein the primary workflow defines imaging settings for the first plurality of medical images;

collecting, using the image acquisition device, at least one of the first plurality of medical images;

receiving a secondary workflow command from a user after collecting the at least one of the first plurality of medical images;

suspending the primary workflow in response to receiving the secondary workflow command and in response to collecting the one or more images corresponding to the first plurality of medical images;

presenting, in response to the secondary workflow command, a plurality of secondary workflows associated with the primary workflow for selection by a user;

receiving a second selection of a second workflow of the plurality of secondary workflows from the user, the secondary workflow corresponding to a second plurality of medical images for a second type of medical examination different from the first type of medical examination, wherein the secondary workflow defines an image sequence for the second plurality of medical images, and wherein the secondary workflow defines imaging settings for the second plurality of medical images;

in response to completion of the collection of the second plurality of medical images, collecting the second plurality of medical images; and resuming the collection of the first plurality of medical images.

* * * * *